United States Patent [19]

Bowser et al.

[11] 4,283,946
[45] Aug. 18, 1981

[54] SAMPLING PROBE FOR GRANULAR MATERIAL

[75] Inventors: Milford D. Bowser, Savage; Vallace W. Vandre, Minneapolis, both of Minn.

[73] Assignee: Cargill, Incorporated, Minneapolis, Minn.

[21] Appl. No.: 860,754

[22] Filed: Dec. 15, 1977

[51] Int. Cl.³ .............................................. G01N 1/14
[52] U.S. Cl. ................. 73/864.31; 73/864.33; 73/864.64
[58] Field of Search ............... 73/423 R, 425.2

[56] References Cited
U.S. PATENT DOCUMENTS
4,088,025  5/1978  Foster et al. .................. 73/423 R Primary Examiner—S. Clement Swisher
Attorney, Agent, or Firm—Fitch, Even, Tabin, Flannery & Welsh

[57] ABSTRACT

A sampling probe is disclosed for obtaining a sample of granular material from a bulk quantity of such material to facilitate inspection of the sample. The probe includes a sampling tube assembly operative to receive a granular sample therein when inserted into a bulk quantity of grain or the like, the sampling tube assembly being operative to isolate the sample and thereafter discharge the sample into a mixing chamber from which the sample is withdrawn through a delivery tube for transfer to an inspection site.

19 Claims, 4 Drawing Figures

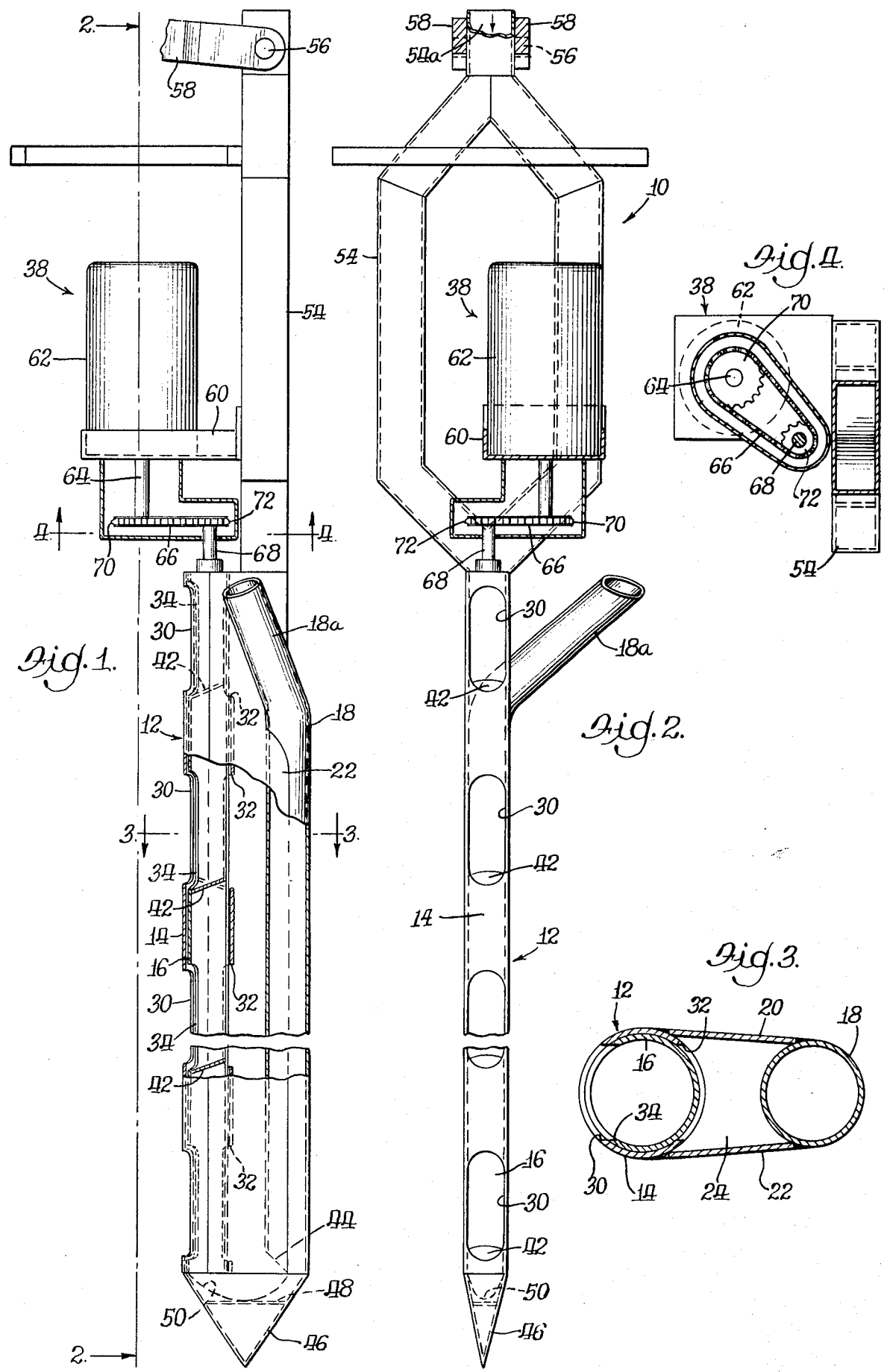

SAMPLING PROBE FOR GRANULAR MATERIAL

The present invention relates generally to sampling probes, and more particularly to an improved sampling probe for obtaining samples of granular material uniformly through the depth of a bulk quantity of granular material wherein the probe is adapted to isolate the samples from the granular mass so as to obtain an unbiased sample for transfer to an inspection site.

It is a common practice in conveying granular materials in bulk quantities, such as in the bulk transfer of grain in trucks and train cars, to take samples of the granular material for inspection and testing. One technique frequently used employs a pneumatic probe having a nozzle which is inserted into the bulk granular material to facilitate withdrawal of a sample by suction into a pneumatic conveying system for transfer to an inspection station. This technique exhibits a major drawback in that it favors the withdrawal of light small granular particles such that the sample is biased in the amount of small, broken and foreign material making up the sample. It is readily apparent that inspection of such a poorly constituted sample will not result in a test analysis truly representative of the bulk quantity of grain material being inspected.

One of the primary objects of the present invention to overcome the disadvantages in the prior sampling probes through the provision of a novel sampling probe which facilitates obtaining more representative samples of granular material generally uniformly throughout the depth of a bulk quantity of granular material, with the result that the sample conveyed to an inspection station is more representative of the granular mass from which the sample is obtained.

Another object of the present invention is to provide a sampling probe which separates the process of obtaining granular samples from a bulk quantity of granular material into two separate stages, a sampling stage which facilitates obtaining unbiased samples uniformly through the depth of the bulk quantity of granular material, and a delivery stage during which the sample is isolated from the remaining grain mass thereby preventing any alteration of the sample contents.

Still another object of the present invention is to provide a novel sampling probe which may be inserted into a bulk quantity of granular material, and which includes a sample tube assembly operative to obtain unbiased samples of granular material throughout the depth of a granular mass and isolate the samples from the remaining granular mass as the samples are covered to a mixing chamber from which the mixed samples may be withdrawn through a delivery tube while remaining isolated from the granular mass.

A feature of the sampling probe in accordance with the present invention lies in the provision of a novel sampling tube assembly employing inner and outer concentric tubes having selectively registrable openings therein facilitating receipt of granular samples from a bulk quantity of granular material into a plurality of compartments in which the samples are first isolated from the granular mass and then passed to a mixing chamber from which the samples may be conveyed to an inspection station through a delivery tube by pneumatic conveying techniques.

Further objects and advantages of the present invention, together with the organization and manner of operation thereof, will become apparent from the following detailed description of the invention when taken in conjunction with the accompanying drawing wherein like reference numerals designate like elements throughout the several views, and wherein:

FIG. 1 is a foreshortened elevational view of a sampling probe constructed in accordance with the present invention, with portions broken away for clarity;

FIG. 2 is a foreshortened view taken substantially along the line 2—2 of FIG. 1, looking in the direction of the arrows;

FIG. 3 is a transverse sectional view, on an enlarged scale, taken along the line 3—3 of FIG. 1, looking in the direction of the arrows; and FIG. 4 is a sectional view taken substantially along the line 4—4 of FIG. 1, looking in the direction of the arrows.

Referring now to the drawing, and in particular to FIGS. 1 and 2, a sampling probe constructed in accordance with the present invention is indicated generally at 10. The sampling probe 10 is adapted to collect samples of granular material uniformly through the depth of a bulk quantity of granular material such as grain or the like as may be carried in a bulk carrier, such as a truck, employed in conveying bulk quantities of grain from the fields to a mill or packaging site. As will become apparent hereinbelow, the sampling probe 10 provides distinct advantages over the prior art sampling probes in that it provides grain samples which are not biased in the amount of small, broken and foreign material drawn from the granular mass as results with the prior art sampling probes.

Briefly, the sampling probe 10 includes sampling tube means, indicated generally at 12, comprising a pair of coaxial elongated outer and inner sampling tubes, indicated at 14 and 16, respectively, which are rotatable relative to each other and form a sampling tube assembly. The sampling tube means 12 is connected to an elongated delivery tube 18 through a pair of connecting walls 20 and 22 which maintain the delivery tube in substantially parallel relation to the assembled outer and inner sampling tubes 14 and 16 and define a mixing chamber 24 therebetween, as best seen in FIG. 3.

The outer tube 14 of the sampling tube assembly has a plurality of longitudinally aligned openings 30 formed in the peripheral wall thereof in longitudinally spaced relation so as to face outwardly from the mixing chamber 24. The outer sampling tube 14 has a second set of longitudinally aligned and spaced openings 32 formed in the peripheral wall thereof substantially diametrically opposed to the openings 30, the openings 32 opening into the mixing chamber 24. The openings 30 and 32 are elongated, as best seen in FIG. 2, with the openings 32 preferably being slightly longer along their longitudinal axes than openings 30. In the illustrated embodiment, the openings 30 are preferably approximately 3 inches in length and the openings 32 are approximately 3⅜ inches along their major axes, the upper edges of openings 30 and 32 being aligned.

The inner sampling tube 16 has a plurality of longitudinally aligned openings 34 formed in its peripheral wall which are substantially the same size as the openings 32 in the outer sampling tube 14 and are longitudinally spaced so as to facilitate selective registration with either set of openings 30 and 32 in the outer sampling tube. The upper edges of openings 34 are aligned with the upper edges of the openings 30 and 32. The openings 32 and 34 are preferably spaced approximately 2 inches apart along the longitudinal lengths of the outer and inner tubes 14 and 16, while the openings 30, being shorter in length, are spaced apart a slightly greater distance and therefore create a stronger outer shell on the probe.

As will be described more fully hereinbelow, the assembled sampling tube means 12, delivery tube 18 and connecting walls 20 and 22 defining the mixing chamber 24 are adapted to be inserted into a bulk quantity of granular material, such as a grain loaded truck vehicle or the like, for sampling the grain. The sampling probe 10 includes control means, indicated generally at 38, operatively associated with the inner sampling tube 16 so as to effect rotation thereof relative to the outer sampling tube 14 between a first position establishing registration of the openings 34 with the openings 30 in the outer sample tube to facilitate entry of granular material into the sampling tube means 12, and a second position wherein the openings 30 are closed off by the inner tube 16 and the openings 34 are in registration with the openings 32 in the outer sampling tube to discharge the grain sample into the mixing chamber 24 from which the grain sample may be removed through the delivery tube 18 for transfer to an inspection site.

Turning now to a more detailed description of the sampling probe 10, the inner sampling tube 16 defines a plurality of sample receiving compartments longitudinally therealong established between floor plates 42 secured at their peripheral edges to the inner surface of the inner sampling tube. The floor plates 42 are preferably angularly inclined so as to lie in planes subtending substantially 30° angles with planes transverse to the longitudinal axis of the inner tube 16, and are positioned so that the lower edge of each floor plate engages the inner surface of the inner sampling tube at the lower edge of a corresponding elongate opening 34, as best seen in FIG. 1. By establishing internal compartments within the inner sampling tube 16 between the inclined floor plates 42, the various compartments are adapted to receive granular samples therein when the sampling probe is inserted in a bulk quantity of grain and the openings 34 are positioned in registration with the openings 30 in the outer sampling tube 14. Since the openings 34 are slightly longer than the openings 30, the incoming granular material moves in a downward direction as it passes through the aligned openings 30 and 34. When the inner tube 14 is rotated to a position establishing registration of the openings 34 with the openings 32 in the outer sampling tube 14, the inclined floor plates 42 cause the granular samples to be discharged by gravity into the mixing chamber 24.

The connecting plates 20 and 22 extend the full length of the outer sampling tube 14 and are connected thereto along longitudinal edges of the connecting plates. Similarly, the connecting plates are secured at their opposite longitudinal edges to the delivery tube 18 which has a length substantially equal to the sampling tubes 14 and 16. Preferably, the upper end of the delivery tube 18 is inclined angularly outwardly at 18a from the longitudinal axis of the lower portion of the delivery tube so as to facilitate connection of the upper open end to a conventional pneumatic conveying tube (not shown) for withdrawing grain samples from the mixing chamber 24 and conveying them to a remote inspection site. The lower end of the delivery tube 18 terminates adjacent the lower end of the assembled outer and inner sampling tubes 14 and 16 and has an opening 44 therein in open communication with the mixing chamber 24 to facilitate withdrawal of the granular sample material from the mixing chamber.

A pointed end cap or nose piece 46 is secured to the lower ends of the connecting plates 20 and 22 and the corresponding ends of the outer sampling tube 14 and delivery tube 18 so as to close the lower end of the sampling probe and adapt it for penetration into a bulk quantity of granular material for sampling thereof. A cross plate 48 is secured within the end cap 46 and provides a backing for molded putty or the like to establish a curved end surface 50 which hardens and forms the lower end of the mixing chamber 24 and eases entry of the granular sample material through the opening 44 in the delivery tube 18.

The upper ends of the connecting walls 20 and 22 are secured to the lower end of a support frame 54 which, in the illustrated embodiment, is made from square tubing in a generally hexagonal configuration as shown in FIGS. 1 and 2. The upper end of the frame 54 has stub shafts 56 extending outwardly from opposite sides thereof adapted for pivotal connection with the bifurcated end of a boom, a portion of which is indicated at 58. The tubular frame 54 is in communication with the upper end of the mixing chamber 24 and has an upper open end, indicated at 54a, open to atmosphere to provide an air inlet. The upper ends of the connecting walls 20 and 22 are closed about the lower end of the tubular frame 54 so that air passing down the support frame 54 passes into the mixing chamber 24 and up through the delivery tube 18. Granular samples passing into the mixing chamber from the compartmentalized inner tube 16 are mixed with the conveying air and passed through the opening 44 upwardly through the delivery tube.

The frame 54 has a generally U-shaped bracket 60 mounted therein which supports a control motor 62. The control motor 62 may comprise a suitably hydraulic or electric motor having a drive shaft 64 which may be selectively rotated in desired angular increments. The motor drive shaft 64 is connected through a suitable sprocket chain 66 to an upwardly extending shaft 68 secured to the upper end of the inner sampling tube 16, the sprocket chain being reeved over sprockets 70 and 72 mounted on the motor drive shaft 64 and inner sampling tube shaft 68. The control motor 62 and its associated connection to the inner sampling tube 16 define the control means 38 for the sampling probe 10, and may comprise substantially any conventional mechanism for effecting desired incremental rotation of the inner sampling tube 16 about its longitudinal axis between rotational positions disposed 180° apart. Position switch indicators are preferably built into the control motor 62. Control lines (not shown), either hydraulic fluid pressure conduits or electrical conductors, pass from the control motor 62 along the length of the boom 58 to a remote control station (not shown) to facilitate remote operation of the sampling probe 10 including control of the boom 58 and the angular relation of the sampling probe to the boom so as to effect a downward penetration of the sampling tube into a bulk quantity of granular material for sampling the same.

In operation, the upper end of the delivery tube 18a is connected to a pneumatic conveying system of known design (not shown). The sampling probe 10 is positioned through movement of the boom 58 to overlie a bulk quantity of granular material to be sampled. The inner sampling tube 16 is rotated to a position wherein its openings 34 are in registration with the openings 32 in the outer sampling tube 16, thus clearing the probe and preparing it for penetration. The boom is then lowered vertically so as to effect full penetration of the sampling probe into the granular material. Preferably, the outer and inner sampling tubes 14 and 16 have sufficient longitudinal length, such as approximately 4-5 feet, to facilitate penetration of the sampling probe through substantially the full depth of a granular load to be sampled.

Preferably, the pneumatic conveying system to which the sampling probe 10 is connected is operated continuously during sampling. After inserting the sampling probe 10 into a bulk quantity of granular material, the inner tube 16 is rotated to effect registration of the openings 34 and 30 and expose the various longitudinal compartments within the inner sampling tube 16 to the granular material and facilitate entry into the compartments between the floor plates 42. The inner sampling tube is then rotated 180° through operation of the control motor 62 to close off the openings 30 and establish registration of the openings 34 with the openings 32 facing the mixing chamber 24 to effect discharge of the granular samples into the mixing chamber.

After the granular samples have been discharged into the mixing chamber 24, the samples are mixed into the conveying air stream and passed downwardly to the opening 44 in the lower end of the delivery tube 18 through which the granular samples are withdrawn. The inner surface of the outer sampling tube 14 and the outer surface of the inner sampling tube 16 are closely spaced to restrict air flow between the inner and outer sampling tubes and thereby prevent small, broken or foreign particles from being drawn into the mixing chamber by any pressure differential between the mixing chamber and environmental pressure outside the sampling probe 10. In this manner, granular samples are obtained through the full depth of the granular mass which are true representations of the grain quality.

Thus, in accordance with the present invention, it is seen that a sampling probe is provided which comprises sampling tube means 12 including an elongated sampling tube 14 adapted to be inserted into a bulk quantity of granular material, the sampling tube means being operatively associated with means defining a mixing chamber extending substantially along the full length of the sampling tube 14. The elongated sampling tube has a plurality of openings therein opening outwardly of the tube for receiving a granular sample therein, and has a further plurality of openings communicating with the sample chamber. Means in the form of an inner sample tube 16 are operatively associated with the elongated outer sampling tube for effecting selective registration with the openings 30 and 32 so as to facilitate sequential entry of the granular samples into the elongate sampling tube, close the outer openings of the sampling tube to isolate the withdrawn samples, and thereafter discharge the granular samples into the mixing chamber from which the mixed sample is withdrawn through a delivery tube for transfer to an inspection site.

While a preferred embodiment of the sampling probe in accordance with the present invention has been illustrated and described, it will be understood to those skilled in the art that changes and modifications may be made therein without departing from the invention in its broader aspects.

Various features of the invention are defined in the following claims.

What is claimed is:

1. A sampling probe for obtaining a sample of granular material from a bulk quantity of such material, said probe comprising, sampling tube means including an elongate sampling tube adapted to be inserted into a bulk quantity of granular material, means operatively associated with said elongate sampling tube and defining a mixing chamber extending substantially along the length of said sampling tube and adapted for insertion into said granular material with said sampling tube, said sampling tube having at least one first opening therein opening outwardly of said tube for receiving a granular sample therein, and having at least one second opening therein communicating with said mixing chamber, said sampling tube means including means operatively associated with said elongate sampling tube for selective registration with said openings therein so as to facilitate sequential entry of granular sample into said elongate sampling tube through said first opening, close said first opening to isolate said sample in said elongate sampling tube, and thereafter effect discharge of said sample into said mixing chamber, and delivery means operatively associated with said mixing chamber to facilitate removal of granular sample therefrom for transfer to an inspection site.

2. A sampling probe as defined in claim 1 wherein said elongate sampling tube comprises an outer sampling tube, said means operatively associated with said elongate sampling tube for selective registration with said openings therein comprising an inner elongate sampling tube disposed coaxially within said outer sampling tube and adapted to be inserted into said bulk quantity of granular material, said inner sampling tube being rotatable relative to said outer tube and having at least one opening in the side wall thereof adapted for selective registration with said first opening in said outer sampling tube to facilitate entry of a granular sample into said inner sampling tube, said opening in said inner sampling tube being registrable with said second opening in said outer sampling tube upon selective rotation of said inner sampling tube whereby to facilitate entry of the sample into said mixing chamber.

3. A sampling probe as defined in claim 2 wherein said delivery means comprises an elongate delivery tube disposed substantially parallel to said sampling tube means, said means defining a mixing chamber comprising wall means interconnecting said elongate sampling tube and said delivery tube so as to define said mixing chamber therebetween, said delivery tube having communication with said mixing chamber so as to facilitate withdrawal of a granular sample from said mixing chamber.

4. A sampling probe as defined in claim 2 wherein said inner sampling tube defines a plurality of compartments along its length and has a plurality of openings therein each of which communicates with one of said compartments, said outer sampling tube having a first set of openings therein aligned longitudinally along said outer tube for registration with said openings in said inner sampling tube when said inner and outer sampling tubes are in first relative positions so as to facilitate entry of granular material into said compartments when the probe is inserted in a quantity of said granular material, said outer tube having a second set of openings therein aligned longitudinally along said second tube for registration with said openings in said inner tube when said inner and outer tubes are in second relative positions, said second set of openings being in communication with said mixing chamber to facilitate passage of material from said compartments into said mixing chamber when said inner and outer tubes are in their said second relative positions.

5. A sampling probe as defined in claim 4 wherein said plurality of compartments in said inner tube are defined by floor surfaces spaced axially along said inner tube internally thereof.

6. A sampling probe as defined in claim 5 wherein said floor surfaces are inclined relative to the axis of said inner tube to facilitate passage of granular material from said compartments into said mixing chamber when said inner and outer tubes are in their second relative positions.

7. A sampling probe as defined in claim 4 including control means for effecting relative rotation between said inner and outer tubes.

8. A sampling probe as defined in claim 7 wherein said inner tube includes an actuator shaft extending outwardly from the upper end of said outer tube to facilitate rotation of said inner sampling tube relative to said outer sampling tube.

9. A sampling probe as defined in claim 2 wherein said inner and outer sampling tubes comprise cylindrical tubes disposed in concentric closely spaced relation so as to substantially restrict airflow therebetween.

10. A sampling probe as defined in claim 9 wherein said delivery means comprises a delivery tube, said means defining said mixing chamber including a pair of plate members connected respectively at their lateral edges to said outer sampling tube and said delivery tube, and including a pointed end piece secured to the bottom edges of said plate members, said delivery tube having an entrance opening located adjacent said pointed end piece in communication with the lower end of said mixing chamber.

11. A sampling probe as defined in claim 5 wherein said compartments are of substantially equal size.

12. A sampling probe as defined in claim 4 wherein said first and second sets of openings in said outer sampling tube are diametrically opposed.

13. A sampling probe as defined in claim 1 including a pointed member secured to the lower end of the probe to facilitate insertion thereof into a bulk quantity of granular material.

14. A sampling probe for obtaining a sample of granular material from a bulk quantity of such material to facilitate inspection of the sample, said probe comprising sampling tube means including a pair of elongate inner and outer tubes, said inner tube being disposed within said outer tube and defining at least one compartment therein, said inner tube having at least one opening therein communicating with said compartment, delivery tube means defining a conveying passage internally thereof, means connecting said sampling tube means and said delivery tube means and defining a mixing chamber therebetween, said inner and outer tubes being rotatable relative to each other and defining first cooperable openings therein facilitating entry of granular material into said compartment when the probe is inserted into a quantity of granular material and when said inner and outer tubes are in first positions relative to each other, said inner and outer tubes being relatively rotatable to second positions blocking entry of granular material into said compartment and defining second cooperable openings facilitating passage of granular material from said compartment into said mixing chamber, said delivery tube means having an entrance opening communicating with said conveying passage and with said mixing chamber to facilitate entry of granular material from said mixing chamber into said conveying passage, said delivery tube means having a transfer opening therein communicating with said conveying passage and facilitating removal of said granular sample material from said conveying passage, and means operatively associated with said sampling tube means for effecting rotation of said inner and outer tubes between their said first and second positions relative to each other.

15. Apparatus comprising:
sampling means for taking a sample from a container of granular material;
means for transferring said sample from said sampling means into a receiving chamber;
a tube connected to said receiving chamber; and
pneumatic means for removing said sample from said receiving chamber through said tube.

16. Apparatus as defined in claim 15 wherein said pneumatic means comprises a vacuum means for creating less than atmospheric pressure in said tube.

17. A sampling device comprising:
a first tube having at least one opening in one side thereof;
a second tube disposed within said first tube, a port formed in said second tube, said second tube having a first position with respect to said first tube whereby said port is in communication with the opening in said first tube and a second position whereby said port is not in communication with the opening in said first tube, and a partition connected to said second tube, said partition having an angled surface thereon that extends from the inside wall of said second tube below the bottom of said port in said second tube, upwardly to the opposite inside wall of said second tube;
an opening disposed in the other side of said first tube whereby said opening in said other side of the first tube is in communication with said port of said second tube when the second tube is in said second position;
a vacuum tube connected to said sampling device and having an opening therein;
pneumatic means connected to said vacuum tube for creating a less than atmospheric pressure in said vacuum tube;
means for receiving a sample of material from said sampling device; and
connecting chamber means for connecting the receiving means with said vacuum tube opening.

18. The sampling device of claim 17 including:
a second opening in said one side of said first tube;
a second port disposed in said second tube and a second partition connected to said second tube, said second partition having an angled surface thereon that extends from the inside wall of said second tube just below the bottom of said second port, upwardly to the opposite inside wall of said second tube.

19. The sampling device of claim 17 including means connected to said second tube for rotating said second tube between said first and second positions thereof.

* * * * *